United States Patent
Shelach

(10) Patent No.: US 10,632,123 B2
(45) Date of Patent: Apr. 28, 2020

(54) USE OF BRAF INHIBITORS FOR TREATING CUTANEOUS REACTIONS

(71) Applicant: Lutris Pharma Ltd., Tel Aviv (IL)

(72) Inventor: Noa Shelach, Tel Aviv (IL)

(73) Assignee: Lutris Pharma Ltd., Tel Aviv (IL)

( * ) Notice: Subject to any disclaimer, the term of this patent is extended or adjusted under 35 U.S.C. 154(b) by 0 days.

(21) Appl. No.: 16/119,263

(22) Filed: Aug. 31, 2018

(65) Prior Publication Data

US 2018/0369247 A1 Dec. 27, 2018

Related U.S. Application Data

(63) Continuation of application No. PCT/IL2017/050301, filed on Mar. 9, 2017.

(60) Provisional application No. 62/306,147, filed on Mar. 10, 2016.

(51) Int. Cl.

| *A61K 31/52* | (2006.01) |
|---|---|
| *A61K 31/506* | (2006.01) |
| *A61K 31/517* | (2006.01) |
| *A61K 31/404* | (2006.01) |
| *A61K 31/44* | (2006.01) |
| *A61K 31/4439* | (2006.01) |
| *A61K 31/4375* | (2006.01) |
| *A61K 31/519* | (2006.01) |
| *A61P 17/00* | (2006.01) |
| *A61K 9/00* | (2006.01) |
| *A61K 31/167* | (2006.01) |

(52) U.S. Cl.
CPC ............ *A61K 31/52* (2013.01); *A61K 9/0014* (2013.01); *A61K 9/0053* (2013.01); *A61K 31/167* (2013.01); *A61K 31/404* (2013.01); *A61K 31/4375* (2013.01); *A61K 31/44* (2013.01); *A61K 31/4439* (2013.01); *A61K 31/506* (2013.01); *A61K 31/517* (2013.01); *A61K 31/519* (2013.01); *A61P 17/00* (2018.01)

(58) Field of Classification Search
CPC ...... A61K 31/52; A61K 31/404; A61K 31/44; A61K 31/4439; A61K 31/4375; A61K 31/519; A61K 9/0014; A61K 31/167; A61P 17/00

See application file for complete search history.

(56) References Cited

U.S. PATENT DOCUMENTS 5,753,612 A * 5/1998 Mitrani .................... A61K 8/64
514/18.6

FOREIGN PATENT DOCUMENTS

WO 2015/171833 A1 11/2015

OTHER PUBLICATIONS

International Search Report and Written Opinion from International Application No. PCT/IL2017/050301 dated Jun. 25, 2017.
Ocvirk et al., "A review of the treatment options for skin rash induced by EGFR-targeted therapies: evidence from randomized clinical trials and a metaanalysis"; Radiology and Oncology, 47(2), pp. 166-175, 2013.
Manousaridis et al., "Cutaneous side effects of inhibitors of the RAS/RAF/MEK/ERK signalling pathway and their management", Journal of the European Academy of Dermatology and Venereology, 27(I), pp. 11-18, 2013.
Gencler et al., "Cutaneous Side Effects of BRAF Inhibitors in Advanced Melanoma: Review of the Literature", Dermatology Research and Practice, 2016.

* cited by examiner

*Primary Examiner* — Sahar Javanmard
(74) *Attorney, Agent, or Firm* — Greenberg Traurig, LLP

(57) ABSTRACT

The invention discloses compositions comprising BRaf inhibitors and uses thereof for treating and/or preventing by topical or systemic administration cutaneous conditions caused by treatment with EGFR inhibitors and/or PI3K inhibitors.

12 Claims, 6 Drawing Sheets

USE OF BRAF INHIBITORS FOR TREATING CUTANEOUS REACTIONS

CROSS REFERENCE TO RELATED APPLICATIONS

This application is a continuation of PCT/IL2017/050301, filed Mar. 9, 2017, which claims priority to and the benefit of U.S. Provisional Patent Application Ser. No. 62/306,147, filed on Mar. 10, 2016, the entire contents of each of which are hereby incorporated by reference in their entireties.

FIELD OF THE INVENTION

The invention relates to compositions comprising BRaf inhibitors and uses thereof for treating and/or preventing cutaneous reaction caused by treatment with EGFR inhibitor and/or PI3K inhibitors.

BACKGROUND

The epidermal growth factor receptor (EGFR) is a receptor tyrosine kinase of the ErbB family. Activation of EGFR leads to homodimerization/heterodimerization, phosphorylation of specific tyrosine residues, and recruitment of several proteins at the intracellular portion of the receptors. In response, downstream signaling pathways, such as the Ras/Raf/MAPK pathway and/or the PI3K pathway may be activated, to further affect cellular targets, including nuclear activation of genes related with cell proliferation, survival, invasion, and metastasis. As such, Epidermal Growth Factor Receptor (EGFR) signaling pathways are involved in various proliferative conditions, in which the EGFR is abnormally activated. Various therapeutic agents which target these pathways are used in the treatment of various related disease, such as, lung cancer, colorectal cancer, head and neck cancer and pancreatic cancer. The therapeutic agents (inhibitors) include monoclonal antibodies (such as cetuximab, panitumumab), which are directed at the extracellular domain of the EGFR, and small-molecule tyrosine kinase inhibitors (such as gefitinib, erlotinib, lapatinib), which are competitive inhibitors of the receptor's tyrosine kinase.

The ability of EGFR inhibitors to block specific molecular pathways driving uncontrolled cellular division in cancer has resulted in a decreased incidence of serious systemic adverse events associated with chemotherapy. However, cutaneous adverse events to EGFR inhibitors have been reported, probably due to the abundant expression of EGFR in the skin and adnexal structures. Cutaneous adverse reactions to EGFR inhibitors include acneiform (papulopustular) rash, abnormal scalp, facial hair and/or eyelash growth, paronychia with or without pyogenic granulomas and telangiectasia.

BRaf is a signal transduction protein kinase involved in the regulation of the mitogen-activated protein kinase (MAPK or ERK) signaling pathway. Mutations in BRaf can induce constitutive signaling through the MAPK (MAPK) pathway which may result in uncontrolled cell proliferation. Use of BRaf inhibitors has been demonstrated to be associated with inhibition of MAPK signaling, as can be determined by inhibition or reduction in level of phosphorylated ERK, which is the downstream effector of BRaf. Yet, it has been further observed that paradoxically, BRaf inhibitors can induce an opposite effect of activation of MAPK signaling in BRaf wild-type cells (as determined by increased levels of phosphorylated ERK).

There is thus a need in the art for effective compositions that can be used to ameliorate or prevent the cutaneous adverse reaction of EGFR inhibitors or PI3K inhibitors in subjects treated with such inhibitors.

SUMMARY

According to some embodiments, there are provided compositions which include a therapeutically effective amount of BRaf inhibitor(s) and uses thereof for the treatment or prevention of cutaneous reaction/condition induced by, associated with or caused by EGFR inhibitors in subjects treated with the EGFR inhibitors. In some embodiments, the cutaneous reaction/condition is induced by, associated with or caused by PI3K inhibitors. In some embodiments, the compositions that include BRaf inhibitors may be systemically or topically administered. In some exemplary embodiments, the compositions that include BRaf inhibitors are topically administered to an affected skin region. In some embodiments, the cutaneous reactions include such conditions as, but not limited to: acneiform (papulopustular) rash, abnormal scalp growth, abnormal facial growth, abnormal hair growth, abnormal eyelash growth, paronychia with or without pyogenic granulomas and telangiectasia.

According to some embodiments, there is provided a method of treating cutaneous adverse reaction caused by EGFR inhibitor treatment of a subject in need thereof, the method comprising administration of a therapeutically effective amount of a BRaf-inhibitor or a pharmaceutical composition comprising the same.

According to some embodiments, there is provided a method of preventing cutaneous adverse reaction caused by EGFR inhibitor treatment of a subject in need thereof, the method comprising administration of a therapeutically effective amount of a BRaf-inhibitor or a pharmaceutical composition comprising the same.

According to some embodiments, there is provided a method of treating cutaneous condition caused by PI3K inhibitor treatment of a subject in need thereof, the method comprising administration of a therapeutically effective amount of a BRaf-inhibitor or a pharmaceutical composition comprising the same.

According to some embodiments, there is provided a method of preventing a cutaneous condition caused by PI3K inhibitor treatment of a subject in need thereof, the method comprising administration of a therapeutically effective amount of a BRaf-inhibitor or a pharmaceutical composition comprising the same.

In some embodiments, there is provided use of a composition comprising an effective amount of a BRaf inhibitor for the treatment or prevention of a cutaneous adverse reaction caused by EGFR inhibitor treatment. In some embodiments, the composition is topically administered.

In some embodiments, there is provided use of a composition comprising an effective amount of a BRaf inhibitor for the treatment or prevention of a cutaneous reaction caused by PI3K inhibitor treatment, wherein the composition is topically administered.

In some embodiments, the BRaf inhibitor may include any suitable agent or drug that can inhibit activity and/or expression of BRaf. In some embodiments, the BRaf inhibitor may be selected from BAY43-9006 (Sorafenib), LGX818 (encorafenib), PLX4032 (vemurafenib), GSK2118436 (dabrafenib), ARQ197 (Tivatinib), GSK1120212 (trametinib), ARQ736, ARQ680, AZ628, CEP-32496, C-1, C-15, C-19, C-A, GDC-0879, NMS-P186, NMS-P349, NMS-P383, NMS-P396, NMS-P730, PLX3603

(RO5212054), PLX4720 (Difluorophenyl-sulfonamine), PF-04880594, PLX4734, RAF265, RO4987655, SB590885, BMS908662, WYE-130600, TAK632, MLN 2480, XL281, and combinations thereof. Each possibility is a separate embodiment.

In some embodiments, the BRaf inhibitor may be selected from C-1, C-15, C-19 and C-A. Each possibility is a separate embodiment.

C-1, C-15, C-19 and C-A are disclosed, for example, in Carnahan et. al. (Mol. Cancer Ther. 2010 August; 9(8):2399-410) and Smith et. al. (J. Med. Chem., 2009, 52 (20), pp 6189-619), and comprise the following molecules structures:

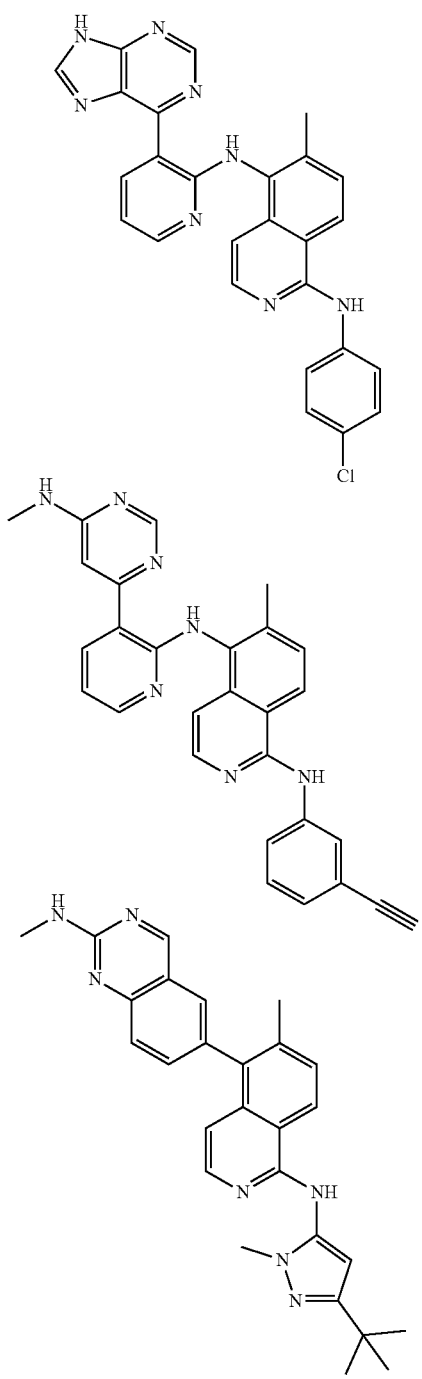

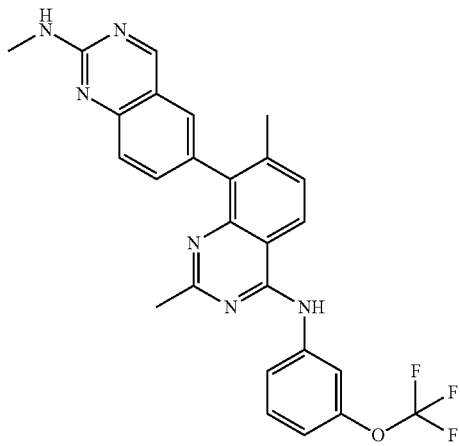

In some embodiments, the BRaf inhibitor exhibits a paradoxical activation of downstream MAPK (ERK).

In some embodiments, the EGFR inhibitor may include any suitable agent or drug that can inhibit activity and/or expression of EGFR. In some embodiments, the EGFR-inhibitor may be selected from: Iressa (gefitinib), Tarceva (erlotinib), Tykerb (Lapatinib), Erbitux (cetuximab), Vectibix (panitumumab), Caprelsa (vandetanib), Portrazza (necitumumab), Tagrisso (osimertinib). Each possibility is a separate embodiment.

In some embodiments, the PI3K inhibitor may include any suitable agent or drug that can inhibit activity and/or expression of PI3K. In some embodiments, the PI3K inhibitor may be selected from GDC-0980 (Apitolisib), GDC-0941 (Pictilisib), BAY 80-6946 (Copanlisib), BKM120 (Puparlisib), NVP-BEZ235 (Dactolisib), IPI 145 (Duvelisib), Idelalisib (GS-1101 or CAL-101), wortmannin and LY294002. Each possibility is a separate embodiment.

In some embodiments, the composition is a pharmaceutical composition. In particular embodiments, the composition is in a form suitable for cosmetic or dermatologic administration.

In some embodiments, the composition is a pharmaceutical composition which includes one or more BRaf inhibitors and a pharmaceutically acceptable carrier.

In some embodiments, the composition is a topical composition. In some embodiments, the topical composition in a form selected from an ointment, cream, gel, hydrogel, foam, spray or a liquid.

According to some embodiments, there is provided a method of treating or preventing a cutaneous condition induced by treatment of a subject in need thereof with an Epidermal Growth like factor receptor (EGFR) inhibitor and/or a Phosphoinositide-3 Kinase (PI3K) inhibitor, the method comprising administration of a BRaf inhibitor to said subject, thereby treating the cutaneous condition.

In some embodiments, the cutaneous condition is selected from acneiform rash, papulopustular rash, abnormal scalp hair growth, abnormal facial hair growth, abnormal hair growth, abnormal eyelash growth, paronychia with or without pyogenic granulomas and telangiectasia. In some embodiments, the cutaneous condition is acneiform rash.

In some embodiments, the subject is treated with an EGFR inhibitor and/or a PI3K inhibitor, prior to administration of the BRaf inhibitor.

In some embodiments, the administration may be selected from topical administration and systemic administration.

In some embodiments, the systemic administration may be selected from enteral administration and parenteral administration. In some embodiments, the systemic administration comprises oral administration.

In additional embodiments, the topical administration may include local administration to the skin of the subject.

According to some embodiments, there is provided a pharmaceutical composition for treating or preventing a cutaneous condition in a subject in need thereof, the composition comprising a therapeutically effective amount of a BRaf inhibitor and a pharmaceutically acceptable carrier, wherein the cutaneous condition is associated with treatment with an EGFR inhibitor and/or a PI3K inhibitor.

In some embodiments, the pharmaceutical composition may be formulated for systemic or local administration.

In some embodiments, the pharmaceutical composition may be formulated for oral administration. In some embodiments, the pharmaceutical composition may be in a dosage form selected from tablet, capsule, liquid, suspension and powder.

In some embodiments, the pharmaceutical composition may be formulated for topical administration. In some embodiments, the pharmaceutical composition may be in a dosage form selected from: ointment, cream, gel, hydrogel, foam, spray, lotion, liquid and dermal patch.

According to some embodiments, there is provided a method of treating or preventing acneiform rash in a subject in need thereof, the method comprising administration of a pharmaceutical composition comprising a therapeutically effective amount of a BRaf inhibitor to the subject to thereby treat acneiform rash in the subject.

According to some embodiments, there is provided a method for identifying or screening out of a BRaf inhibitor population, suitable BRaf inhibitor(s) as candidate(s) for clinical development of drugs for treating and/or preventing cutaneous reaction caused by treatment with EGFR inhibitor and/or PI3K inhibitors, the method comprising:
 (i) providing a population of known or new BRaf inhibitors;
 (ii) measuring the activation of MAPK (ERK) by said BRaf inhibitors;
 (iii) selecting the BRaf inhibitors with the highest paradoxical MAPK activation effect as candidates for clinical development for treating or preventing said cutaneous reaction.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A-Pictogram showing Western Blot analysis of phosphorylated ERK (Phospho-ERK) in HEK cells lysates following treatment with the indicated BRaf inhibitors, negative control (vehicle treated cells (DMSO 0.1%)), positive control (cells treated with growth factors mix (HKGS)), or non-treated cells (untreated); FIG. 1B—Pictogram showing Western Blot analysis of Total ERK in the HEK lysates; FIG. 1C—Bar graphs showing the ratio between phosphorylated ERK and total ERK, based on densitometry analysis of the Western Blots shown in FIGS. 1A-B. Size markers (Kd) are indicated by the numbers to the left of the Blots presented in FIGS. 1A-B;

FIG. 2A—Pictogram showing Western Blot analysis of phosphorylated ERK Phospho-ERK) in HEK cells lysates following treatment with the indicated BRaf inhibitors, negative control (vehicle treated cells (DMSO 0.1%)), positive control (cells treated with growth factors mix (HKGS)), or non-treated cells (untreated); FIG. 2B—Pictogram showing Western Blot analysis of Total ERK in the HEK lysates; FIG. 2C—Bar graphs showing the ratio between phosphorylated ERK and total ERK, based on densitometry analysis of the Western Blots shown in FIGS. 2A-B. Size markers (Kd) are indicated by the numbers to the left of the Blots presented in FIGS. 2A-B;

FIG. 3A—Pictogram showing Western Blot analysis of phosphorylated ERK (Phospho-ERK) in HEK cells lysates following treatment with the indicated BRaf inhibitors, negative control (vehicle treated cells (DMSO 0.1%)), positive control (cells treated with growth factors mix (HKGS)), or non-treated cells (untreated); FIG. 3B—Pictogram showing Western Blot analysis of Total ERK in the HEK lysates; FIG. 3C—Bar graphs showing the ratio between phosphorylated ERK and total ERK, based on densitometry analysis of the Western Blots shown in FIGS. 3A-B. Size markers (Kd) are indicated by the numbers to the left of the Blots presented in FIGS. 3A-B;

FIG. 4A—Pictogram showing Western Blot analysis of phosphorylated ERK (Phospho-ERK) in HEK cells lysates following treatment with the indicated BRaf inhibitors, negative control (vehicle treated cells (DMSO 0.1%)), positive control (cells treated with growth factors mix (HKGS)), or non-treated cells (untreated); FIG. 4B—Pictogram showing Western Blot analysis of Total ERK in the HEK lysates; FIG. 4C—Bar graphs showing the ratio between phosphorylated ERK and total ERK, based on densitometry analysis of the Western Blots shown in FIGS. 4A-B. Size markers (Kd) are indicated by the numbers to the left of the Blots presented in FIGS. 4A-B; FIG. 5A—Bar Graphs showing the relative proliferation (% of vehicle (DMSO 0.1%)) of the cells in the presence of C-1 BRaf inhibitor (concentrations of 0.02 µM, 0.05 µM, 0.14 µM, 0.41 µM, 0.123 µM, 0.37 µM, 1.1 µM, 3.3 µM or 10 µM). FIG. 5B—Bar Graphs showing the relative proliferation (% of vehicle (DMSO 0.1%)) of the cells in the presence of C-15 BRaf inhibitor (concentrations of 0.02 µM, 0.05 µM, 0.1404, 0.41 µM, 0.123 µM, 0.37 µM, 1.1 µM, 3.3 µM or 10 µM); FIG. 5C—Bar Graphs showing the relative proliferation (% of vehicle (DMSO 0.1%)) of the cells in the presence of C-19

BRaf inhibitor (concentrations of 0.02 µM, 0.05 µM, 0.14 µM, 0.41 µM, 0.123 µM, 0.37 µM, 1.1 µM, 3.3 µM or 10 µM); FIG. 5D—Bar Graphs showing the relative proliferation (% of vehicle (DMSO 0.1%)) of the cells in the presence of Vemurafenib BRaf inhibitor (concentrations of 0.02 µM, 0.05 µM, 0.14 µM, 0.41 µM, 0.123 µM, 0.37 µM, 1.1 µM, 3.3 µM or 10 µM).

DETAILED DESCRIPTION

Figure 1A:
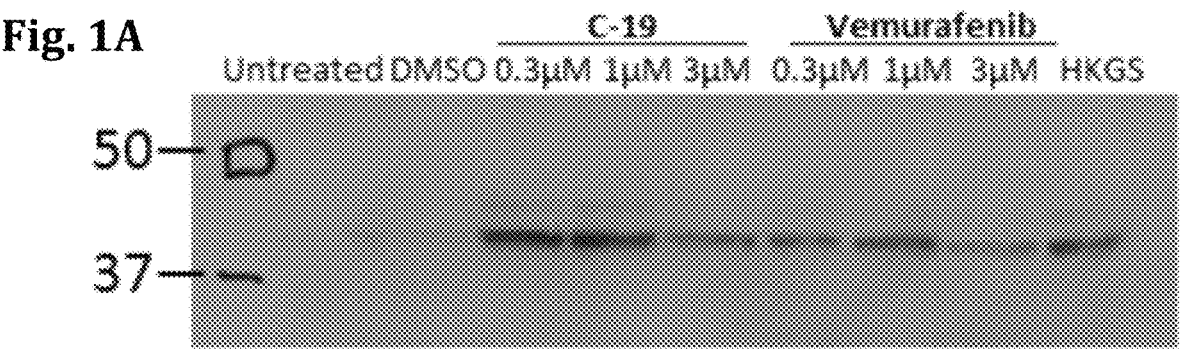
FIGS. 1A-C—Activation of ERK in human primary keratinocytes (HEKa) following treatment with BRaf inhibitors (0.3 µM, 1 µM or 3 µM C-19 or Vemurafenib).

The present invention provides compositions capable of treating or preventing cutaneous reaction induced or caused by treatment with EGFR inhibitor(s) and/or PI3K inhibitor(s), wherein the composition include a therapeutically effective amount of one or more BRaf-inhibitors. In some embodiments, the composition is a topical composition suitable for administration on an affected skin area.

In some embodiments, the present invention provides compositions capable of treating or preventing cutaneous reaction induced or caused by treatment with EGFR inhibitor(s), wherein the composition include a therapeutically effective amount of one or more BRaf-inhibitors.

In some embodiments, the cutaneous reaction induced or caused by treatment with EGFR inhibitor may be selected from: acneiform (papulopustular) rash, abnormal scalp growth, abnormal facial growth, abnormal hair growth, abnormal eyelash growth, Paronychia with or without pyogenic granulomas and telangiectasia. In some exemplary embodiments, the skin condition is acneiform rash. In some embodiments, the condition is acneiform rash.

According to some embodiments, there are provided compositions which include therapeutically effective amount of BRaf inhibitor(s) and uses thereof for the treatment or prevention of cutaneous reaction induced or caused by EGFR inhibitors in subjects treated with the EGFR inhibitors. In some embodiments, the compositions that include BRaf inhibitors are topically administered. In some embodiments, the cutaneous reaction include such conditions as, but not limited to acneiform (papulopustular) rash, abnormal scalp growth, abnormal facial growth, abnormal hair growth, abnormal eyelash growth, Paronychia with or without pyogenic granulomas and telangiectasia.

In some embodiments, the present invention provides compositions capable of treating or preventing cutaneous reaction induced or caused by treatment with PI3K inhibitor(s), wherein the composition include a therapeutically effective amount of one or more BRaf-inhibitors. In some embodiments, the composition is a topical composition suitable for administration on an affected skin area. In some embodiments, the cutaneous reaction induced or caused by treatment with PI3K inhibitor may be selected from acneiform (papulopustular) rash, abnormal scalp growth, abnormal facial growth, abnormal hair growth, abnormal eyelash growth, Paronychia with or without pyogenic granulomas and telangiectasia. In some exemplary embodiments, the skin condition is acneiform rash. In some embodiments, the condition is acneiform rash.

According to some embodiments, there are provided compositions which include a therapeutically effective amount of BRaf inhibitor(s) and uses thereof for the treatment or prevention of cutaneous reaction induced or caused by PI3K inhibitor(s) in a subject treated with the PI3K inhibitor(s). In some embodiments, the compositions that include BRaf inhibitors are topically administered. In some embodiments, the cutaneous reaction include such conditions as, but not limited to acneiform (papulopustular) rash, abnormal scalp growth, abnormal facial growth, abnormal hair growth, abnormal eyelash growth, paronychia with or without pyogenic granulomas and telangiectasia.

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As used herein, the terms "BRAF", "B-Raf", "Braf" and "BRaf" may be used interchangeably. The terms relate to serine/threonine-protein kinase BRaf, which is involved is cellular signaling pathways. The term inhibitor with respect to BRaf is directed to any one or more agent (drug), compound or molecule that can affect activity and/or expression of a WT or mutated BRaf. The inhibitor may be selective or non-selective. In some embodiments, the inhibitor may exhibit a paradoxical MAPK effect, in which the inhibitor induces increased MAPK activity, for example, in cells where the target BRaf is a WT BRaf inhibitors are known in the art. For example, US Patent application Publication No. US 20130156768 discloses such inhibitors. For example, Carnahan et. al. (Mol. Cancer Ther. 2010 August; 9(8):2399-410) and Smith et. al. (J. Med. Chem., 2009, 52 (20), pp 6189-619), disclose BRaf inhibitors. In some embodiment, the BRaf inhibitor may include the compound, a derivative thereof, an acceptable salt thereof and/or a solvate thereof.

As used herein, the term "EGFR", relates to Epidermal Growth Factor Receptor (EGFR) which is a receptor tyrosine kinase of the ErbB family that is involved is cellular signaling pathways. The term inhibitor with respect to EGFR is directed to any one or more agents (drugs), compounds or molecules that can affect activity and/or expression of a WT or mutated EGFR. The inhibitor may be selective or non-selective.

As used herein, the terms "PI3K" relates to phosphoinositide-3 kinase proteins. PI3K proteins catalyze the production of lipid second-messengers from phosphoinositide-2 phosphate into phosphoinositide triphosphate in cellular membranes. The phosphoinositide-3 kinase/protein kinase-B/mammalian target of rapamycin (PI3K/AKT/mTOR) pathway is a key signaling pathway for important cellular functions such as growth control, metabolism and translation initiation. The term inhibitor with respect to PI3K is directed to any one or more agent (drug), compound or molecule that can affect activity and/or expression of a WT or mutated PI3K. The inhibitor may be selective or non-selective.

As used herein, the terms "cutaneous reaction", "cutaneous adverse reaction" and "cutaneous condition" may interchangeably be used and are directed to a skin (cutaneous) condition that has developed/arose/initiated/induced/caused/evolved as a result of treatment with EGFR inhibitor and/or PI3K inhibitor. In some embodiments, the skin condition is a side effect of the treatment with the EGFR inhibitor. In some embodiments, the skin condition is a side effect of the treatment with the PI3K inhibitor.

As used herein, "therapeutically effective amount" refers to that amount of a pharmaceutical ingredient which substantially induces, promotes or results in a desired therapeutic or preventative effect. In some embodiments, the term refers to the amount of a compound being administered which provides a therapeutic effect for a given condition and administration regimen, specifically an amount which relieves or prevents to some extent one or more of the symptoms of the disorder being treated.

As used herein, "pharmaceutically acceptable carrier" refers to a diluent or vehicle which is used to enhance the delivery and/or pharmacokinetic properties of a pharmaceutical ingredient with which it is formulated, but has no therapeutic effect of its own, nor does it induce or cause any undesirable or untoward effect or adverse reaction in the subject.

As used herein, "pharmaceutical composition" refers to therapeutically effective amounts of the compounds of the present invention, together with suitable (acceptable) diluents, preservatives, solubilizers, emulsifiers, adjuvant and/or carriers.

As used herein, "pharmaceutically acceptable carrier" refers to a diluent or vehicle which is used to enhance the delivery and/or pharmacokinetic properties of a pharmaceutical ingredient with which it is formulated, but has no therapeutic effect of its own, nor does it induce or cause any undesirable or untoward effect or adverse reaction in the subject. Pharmaceutically acceptable carriers are well known to those skilled in the art and include, but are not limited to phosphate buffer and/or saline. Additionally, such pharmaceutically acceptable carriers may be aqueous or non-aqueous solutions, suspensions, and emulsions.

As used herein, the terms "treating" or "treatment" of a cutaneous condition induced by EGFR inhibitors and/or PI3K inhibitors refer to healing, ameliorating, repairing, or restoring the condition. As used herein, the terms "preventing" or "prevention" of a cutaneous condition induced by EGFR inhibitors and/or PI3K inhibitors refer to barring a subject from acquiring the cutaneous condition. In some embodiments, the terms refer to avert or avoid a cutaneous condition from occurring. In some embodiments, preventing is directed to ameliorating the damage associated with the cutaneous condition.

According to some embodiments, the BRaf inhibitor may comprise or consist of any suitable agent or drug that can inhibit activity or expression of BRaf. In some embodiments, the BRaf-inhibitor may be selected from BAY43-9006 (Sorafenib), LGX818 (encorafenib), PLX4032 (vemurafenib), GSK2118436 (dabrafenib), ARQ197 (Tivatinib), GSK1120212 (trametinib), ARQ736, ARQ680, AZ628, C-1, C-15, C-19, C-A, CEP-32496, GDC-0879, NMS-P186, NMS-P349, NMS-P383, NMS-P396, NMS-P730, PLX3603 (RO5212054), PLX4720 (Difluorophenyl-sulfonamine), PF-04880594, PLX4734, RAF265, RO4987655, SB590885, BMS908662, WYE-130600, TAK632, MLN 2480, XL281 and combinations thereof. Each possibility is a separate embodiment.

C-1, C-15, C-19, and C-A, and are disclosed, for example, in, Carnahan et. al. (Mol. Cancer Ther. 2010 August; 9(8): 2399-410) and Smith et. al. (J. Med. Chem., 2009, 52 (20), pp 6189-619), and comprise the following molecules structures:

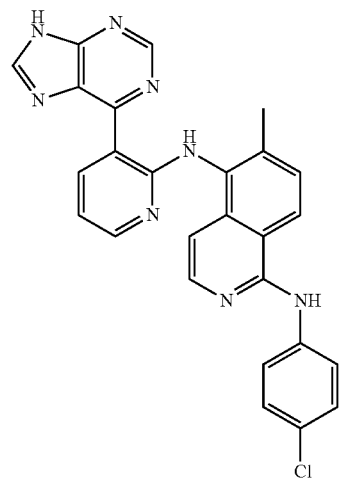

C-1

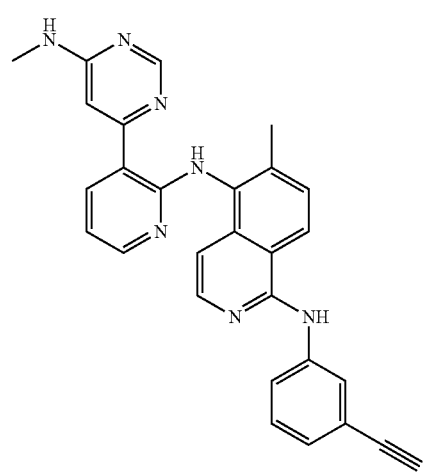

C-15

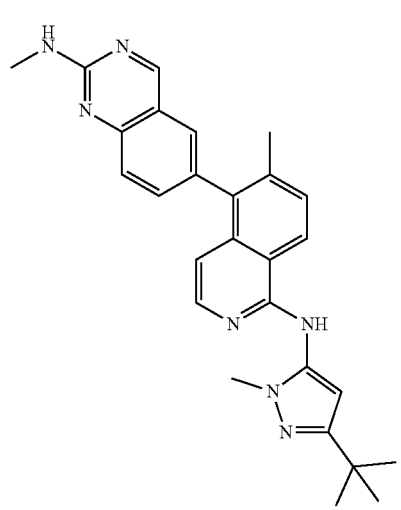

C-19

-continued

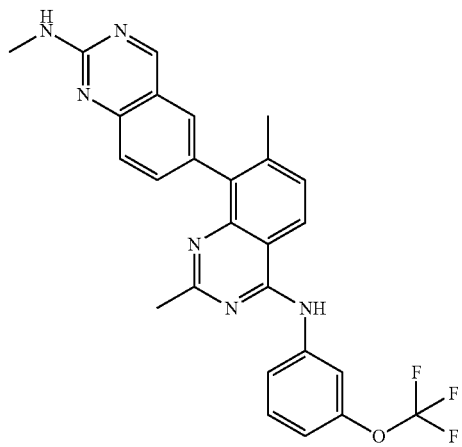

C-A

In some embodiments, the BRaf inhibitor exhibits a paradoxical MAPK activation effect.

In some embodiments, the EGFR inhibitor may comprise or consist of any suitable agent or drug that can inhibit activity and/or expression of EGFR. In some embodiments, the EGFR-inhibitor may be selected from: Iressa (gefitinib), Tarceva (erlotinib), Tykerb (Lapatinib), Erbitux (cetuximab), Vectibix (panitumumab), Caprelsa (vandetanib), Portrazza (necitumumab), Tagrisso (osimertinib) and combinations thereof. Each possibility is a separate embodiment.

In some embodiments, the PI3K inhibitor may comprise or consist of any suitable agent or drug that can inhibit activity and/or expression of PI3K. In some embodiments, the PI3K inhibitor may be selected from GDC-0980 (Apitolisib), GDC-0941 (Pictilisib), BAY 80-6946 (Copanlisib), BKM120 (Puparlisib), NVP-BEZ235 (Dactolisib), Duvelisib (IPI-145), Idelalisib (GS-1101 or CAL-101), wortmannin and LY294002. Each possibility is a separate embodiment. Each possibility is a separate embodiment.

While all the BRaf drugs exhibit BRaf inhibitor activity, the inventor of the present disclosure has found that many are unsuitable for the treatment or prevention of cutaneous reaction caused by treatment with a EGFR inhibitor and/or a PI3K inhibitor.

Without wishing to be bound by theory, the inventor believes that only those BRaf inhibitors which exhibit a paradoxical MAPK effect (MAPK activation) are suitable drug candidates for the treatment or prevention of a cutaneous reaction caused by treatment with a EGFR inhibitor, a PI3K inhibitor or mixtures thereof.

In some embodiments, there are provided BRaf inhibitors which exhibit a paradoxical MAPK effect, suitable for the treatment or prevention of a cutaneous reaction caused by treatment with a EGFR inhibitor, a PI3K inhibitor or mixtures thereof.

It is herein disclosed for the first time that owing to their paradoxical MAPK effect, BRaf inhibitors are useful in treating cutaneous conditions, such as, acneiform rash, which is caused or induced by treatment with a EGFR inhibitor.

In some embodiments, there are provided BRaf inhibitors which exhibit a paradoxical MAPK effect, suitable for the treatment or prevention of a cutaneous reaction caused by treatment with a EGFR inhibitor. In some embodiments, the EGFR inhibitors treatment is anticancer treatment administered to a subject afflicted with cancer.

It is herein further disclosed for the first time that owing to their paradoxical MAPK effect, BRaf inhibitors are useful in treating cutaneous conditions, such as acneiform rash, which is caused or induced by treatment with a PI3K inhibitor.

In some embodiments, there are provided BRaf inhibitors which exhibit a paradoxical MAPK effect (activation of MAPK), suitable for the treatment or prevention of a cutaneous reaction caused by treatment with a PI3K inhibitor. In some embodiments, the PI3K inhibitor treatment is anticancer treatment administered to a subject afflicted with cancer.

The paradoxical MAPK effect may serve as a useful tool for screening of BRaf inhibitors suitable for selection of suitable candidates for treatment or prevention of a cutaneous reaction caused by treatment with a EGFR inhibitor, a PI3K inhibitor or mixtures thereof, out of the multitude of existing or new BRaf inhibitors.

In some embodiments, there is provided a method for screening out of a BRaf inhibitor population, suitable BRaf inhibitors as candidates for clinical development of drugs for treating and/or preventing cutaneous reaction caused by treatment with EGFR inhibitor and/or PI3K inhibitors, the method comprising:
  (i) Providing a population of known or new BRaf inhibitors
  (ii) Measuring the activation of MAPK (ERK) by said BRaf inhibitors (see Example 1 hereinbelow)
  (iii) Selecting the BRaf inhibitors with the highest paradoxical MAPK activation effect as candidates for clinical development.

In some embodiments, the composition for use in the invention comprises a therapeutically effective amount of one or more BRaf inhibitors, and a pharmaceutically acceptable carrier. In some embodiments, the pharmaceutical composition includes at least one BRaf inhibitor and a pharmaceutically acceptable carrier.

In some embodiments, the pharmaceutical composition may be formulated in any of a number of forms suitable for systemic or topical administration.

In some embodiments, the composition for use in the invention comprises a therapeutically effective amount of one or more BRaf inhibitors, and a pharmaceutically acceptable carrier and may be systemically or topically administered. In some embodiments, the pharmaceutical composition includes at least one BRaf inhibitor and a pharmaceutically acceptable carrier. In some embodiments, the pharmaceutical composition may be formulated in any of a number of forms suitable for systemic administration. In some embodiments, the systemic administration may be selected from enteral and parenteral administration.

In some embodiments, the preparing the pharmaceutical composition, the BRaf inhibitor may be suitably formulated as inclusion complexes, nanoemulsions and microemulsions.

In some embodiments, the pharmaceutical composition may be formulated in any of a number of forms suitable for dermatological, topical and/or local administration, such as for example, a gel, a suspension, an ointment, a lotion, a liquid, a solution, an emulsion or microemulsion, a film, a cement, a powder, a glue, an aerosol, a spray, a foam, a patch, a bandage, and the like and combinations thereof. Each possibility is a separate embodiment.

In some embodiments, the dosage administered and/or the dosage regime is dependent upon the age, health, weight, severity of the cutaneous condition of the subject, the use of treatment with EGFR inhibitors and/or PI3K inhibitors, frequency of treatment, and the nature of the desired effect. Each possibility is a separate embodiment.

In some embodiments, the amount and nature of the BRaf inhibitor in any unit dosage form comprises a therapeutically effective amount which may vary depending on the recipient subject, frequency of administration, the EGFR and/or PI3K inhibitor(s) treatment, site and severity of the cutaneous condition, and the like. Each possibility is a separate embodiment.

In some embodiments, the concentration, amount or percentage of BRaf inhibitors in the formulation may vary widely, and may depend on the volume, viscosity, dosage form, etc. of the formulation, as well as the administration regime. For example, in some embodiments, the concentration of the BRaf inhibitor may vary between 0.5 nM to 1000 nM and any subranges thereof. Each possibility is a separate embodiment. For example, in some embodiments, the amount of the BRaf inhibitor may vary between 0.5 μg to 1000 mg and any subranges thereof. Each possibility is a separate embodiment. In some embodiments, the amount of the BRaf inhibitor may be in the range of 200-1000 micrograms. For example, in some embodiments, the percentage of the BRaf inhibitor may be in the range of, 0.005-5% of the formulation, and any subranges thereof. Each possibility is a separate embodiment. In some embodiments, the percentage of the BRaf inhibitor may be in the range of, 0.01-3%. In some embodiments, the percentage of the BRaf inhibitor may be in the range of, 0.1-3%.

In some embodiments, the pharmaceutical composition may further include at least one additional therapeutic agent capable of affecting the cutaneous condition.

In some embodiments, the pharmaceutical compositions of the invention may be manufactured in a manner which is itself known to one skilled in the art, for example, by means of conventional mixing, granulating, dragee-making, softgel encapsulation, dissolving, extracting, or lyophilizing processes.

In some embodiments, the BRaf inhibitor may be administered with one or more therapeutic agents, in a single composition or in separate compositions. Each possibility is a separate embodiment.

In some embodiments, the BRaf inhibitor (or a pharmaceutical composition comprising the same) may be administered prior to, concomitantly with, or after administration of an additional therapeutic agent (or a pharmaceutical composition comprising the same). Each possibility is a separate embodiment.

In some embodiments, the pharmaceutical composition may be delivered in a controlled release system.

In some embodiments, the BRaf inhibitors can be administered to using any available conventional methods and routes suitable for delivery of conventional drugs, including systemic or localized routes. In general, routes of administration contemplated by the invention include, but are not necessarily limited to, enteral, parenteral, or inhalational routes.

In some embodiments, parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery. Where systemic delivery is desired, administration can typically involve invasive or systemically absorbed topical or mucosal administration of pharmaceutical preparations.

In some embodiments, the BRaf inhibitors can also be delivered to the subject by enteral administration. Enteral routes of administration include, but are not necessarily limited to, oral and rectal (e.g., using a suppository) delivery.

According to some embodiments, administering is administering topically. According to some embodiments, the composition is formulated for topical administration to body surfaces. Non-limiting examples of formulations for topical use include cream, ointment, lotion, gel, foam, suspension, aqueous or cosolvent solutions, salve and sprayable liquid form. Other suitable topical product forms for the compositions of the present invention include, for example, emulsion, mousse, foam, lotion, solution and serum. Additional suitable topical product forms include patches, bandages, and the like.

In some embodiments, the pharmaceutical composition can be in solid or liquid form such as tablets, powders, capsules, pellets, solutions, suspensions, elixirs, emulsions, gels, creams, or suppositories. Pharmaceutically acceptable carriers include gums, starches, sugars, cellulosic materials, and mixtures thereof. The preparation can also be administered by intravenous, intra-arterial, or intramuscular injection of a liquid preparation, oral administration of a liquid or solid preparation, or by topical application. Administration can also be accomplished by use of a rectal suppository.

The preparation of pharmaceutical compositions which contain an active component is well understood in the art. Typically, such compositions are prepared as aerosols of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof.

In some embodiments, in addition, if desired, the composition can contain minor amounts of auxiliary substances such as wetting or emulsifying agents, pH buffering agents, which enhance the effectiveness of the active ingredient.

In some embodiments, an active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, methanesulfonic, benzene sulfonic, naphthalene sulfonic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, the active compound can be delivered in a vesicle, such as, for example, a liposome.

In some embodiments, for topical administration to body surfaces (such as, skin), for example, creams, ointments, gels, lotions, solutions, co-solvent solutions, suspensions, patches, bandages, liquids, foams and the like may be used. The BRaf inhibitors or their physiologically tolerated derivatives such as salts, hydrates, and the like are conveniently prepared and applied as solutions, suspensions, or emulsions in a physiologically acceptable diluent with or without a pharmaceutical carrier.

According to some embodiments, there are provided kits with unit doses of suitable BRaf inhibitors, such as, oral doses, injectable doses, or topical doses.

According to some embodiments, in such kits, in addition to the containers containing the unit doses, an informational package insert describing the use and attendant benefits of the BRaf inhibitors in treating the cutaneous condition.

According to some embodiments, there is provided a kit for use in treating or preventing a cutaneous condition induced, caused, or associated with treatment with EGFR inhibitor, the kit includes a composition comprising a therapeutically effective amount of a BRaf-inhibitor and instructions for use. In some embodiments, the composition is a pharmaceutical composition. In some embodiments, the pharmaceutical compositions is provided in a suitable dosage form. In some embodiments, the dosage form is selected from systemic and topical. In some embodiments, the topical dosage form may be selected from, but not limited to: ointment, cream, gel, hydrogel, spray, dermal patch, lotion, bandage, liquid, or any combinations thereof. Each possibility is a separate embodiment. In some embodiments, the systemic dosage form is oral form, selected from, but not limited to: tablet, capsule, liquid, suspension and powder, or any combination thereof. Each possibility is a separate embodiment.

According to some embodiments, there is provided a kit for use in treating or preventing a cutaneous condition induced, caused, or associated with treatment with PI3K inhibitor, the kit includes a composition comprising a therapeutically effective amount of a BRaf-inhibitor and instructions for use. In some embodiments, the composition is a pharmaceutical composition. In some embodiments, the pharmaceutical composition is provided in a suitable dosage form. In some embodiments, the dosage form is selected from systemic and topical. In some embodiments, the topical dosage form may be selected from, but not limited to: ointment, cream, gel, hydrogel, spray, dermal patch, lotion, bandage, liquid, or any combinations thereof. Each possibility is a separate embodiment. In some embodiments, the systemic dosage form is oral form, selected from, but not limited to: tablet, capsule, liquid, suspension and powder, or any combination thereof. Each possibility is a separate embodiment.

The terms "comprises", "comprising", "includes", "including", "having" and their conjugates mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The following examples are presented in order to more fully illustrate some embodiments of the invention. They should, in no way be construed, however, as limiting the broad scope of the invention.

EXAMPLES

Example 1—Activation of MAPK (ERK) by Various BRaf Inhibitors in Human Normal Keratinocytes Cells (HEKa)

In order to determine the effect of various BRaf inhibitors on activation of ERK in relevant keratinocytes cells, the level of ERK phosphorylation was determined in human normal Keratinocytes cells, in response to treatment with the BRaf inhibitors.

Experimental Procedure:

Human normal Keratinocyte cells HEKa were seeded in 10 cm dishes (300,000 cells/dish) and incubated overnight at 37° C., 5% $CO_2$. Next morning, the cells were starved for 2 hours and then treated with the various inhibitors (or control treatments) for 2 hours. Post incubation the cells were lyzed with RIPA Buffer and the protein extracts were analyzed by Western-Blot for detection of phospho ERK and total ERK2, by use of suitable antibodies. Untreated and 0.1% DMSO treated cells were used as negative control. Growth factors mix (HKGS) was used as positive control (Gibco CAT #: S0015).

Western Blot:

7.5 µg of total extract was loaded on 10% or 12% acrylamide gels. Following transfer, the membranes were blocked with TBST/5% skim milk and then incubated with Mouse anti phospho ERK (1:1000 in TBST 5% BSA, ON at 4° C.) and goat anti Mouse HRP (1:10,000 in TBST 5% BSA, 1 hour RT). The membranes were exposed using SuperSignal West Pico Chemiluminescent Substrate. The HRP was then inactivated by incubating the membranes for 1 hour with 0.5% Sodium azide. Following washes and ECL exposure in order to ensure absence of signal, the membranes were reblocked for 15 min with TBST/5% skim milk and then incubated with Rabbit anti total ERK2 (1:500 in TBST 5% BSA, ON at 4° C.), goat anti Rabbit HRP (1:5,000 in TBST 5% BSA, 1 hour RT) and finally exposed using the SuperSignal West Pico Chemiluminescent Substrate. The resulting images (films) were scanned and the signal were quantified using ImageJ software.

BRaf inhibitors used in the experiments included, C-1, C-15, C-19 C-A or vemurafenib, at concentrations of 0.304; 1 µM or 3 µM. ZM (ZM336372) a c-Raf inhibitor, which serves in the present experiments as a Braf activator and was used as a control.

C-1, C-15, C-19, C-A and ZM336372 (control) are disclosed, for example, in, Carnahan et. al. (Mol. Cancer Ther. 2010 August; 9(8):2399-410) and Smith et. al. (J. Med. Chem., 2009, 52 (20), pp 6189-619), and comprise the following molecules structures:

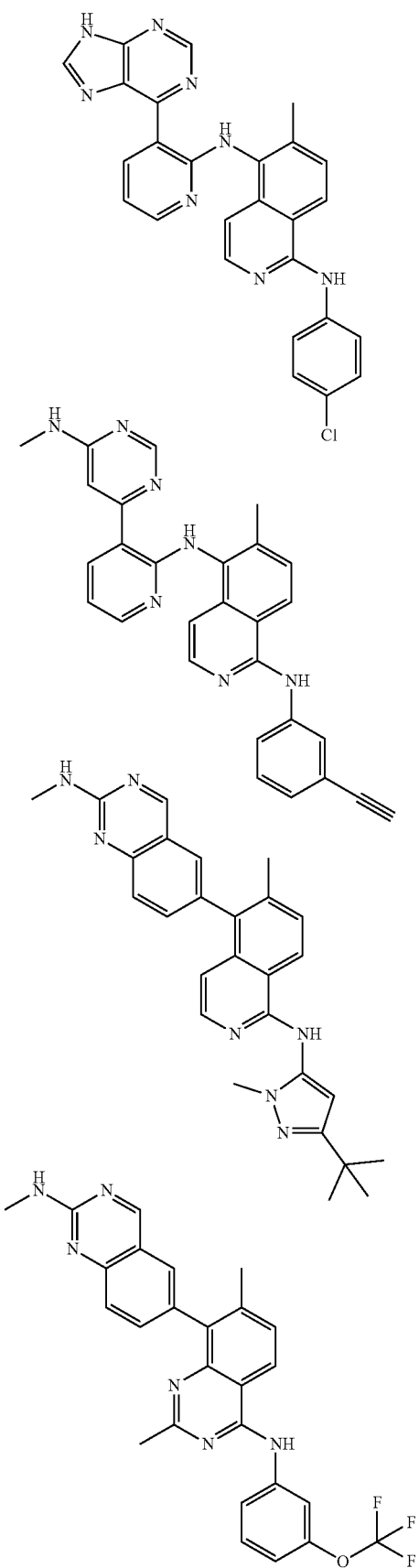

C-1

C-15

C-19

C-A

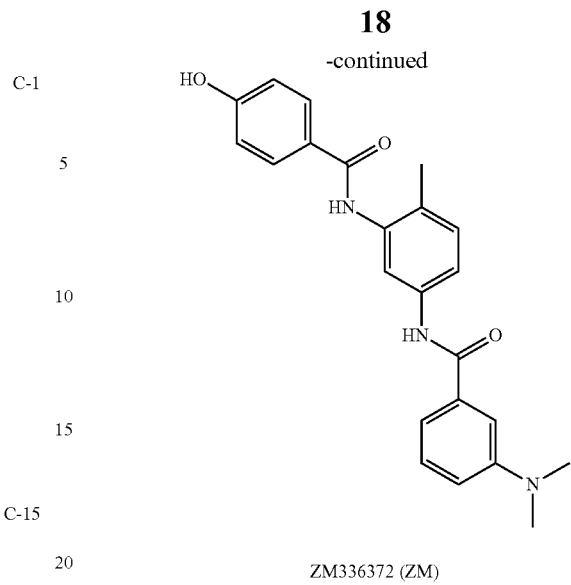

ZM336372 (ZM)

The results are presented in FIGS. 1A-C to 4A-C.

Figure 1B:
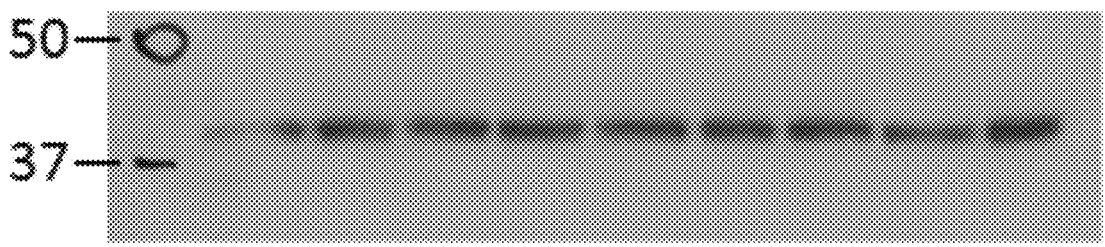
Figure 1C:
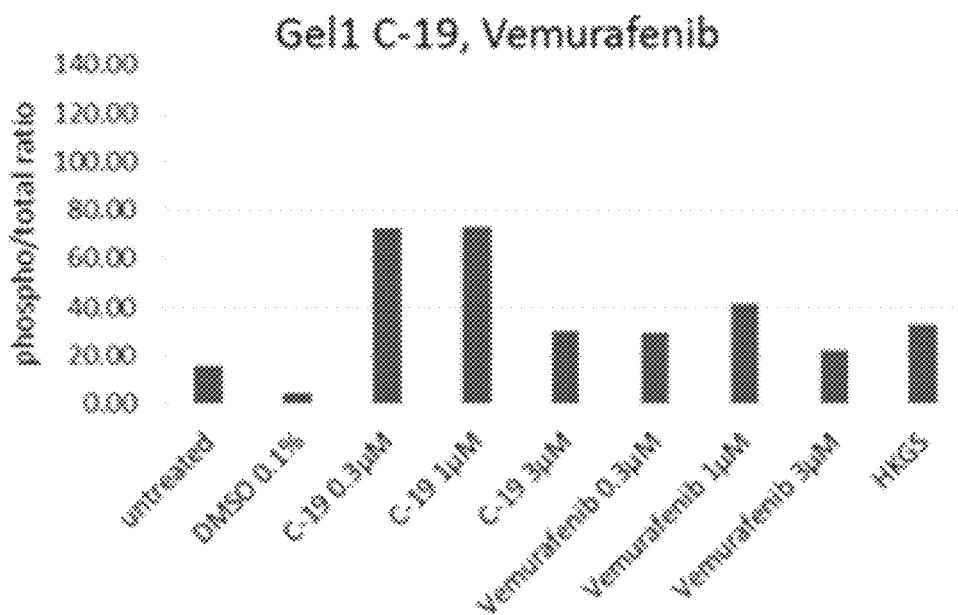

The results shown in FIGS. 1A-C demonstrate the activation of ERK (as determined by increase in relative amount of Phosphorylated ERK) in human primary keratinocytes (HEKa) following treatment with increasing amounts (0.3 µM, 1 µM or 3 µM) of C-19 or Vemurafenib BRaf inhibitors.

Figure 2A:
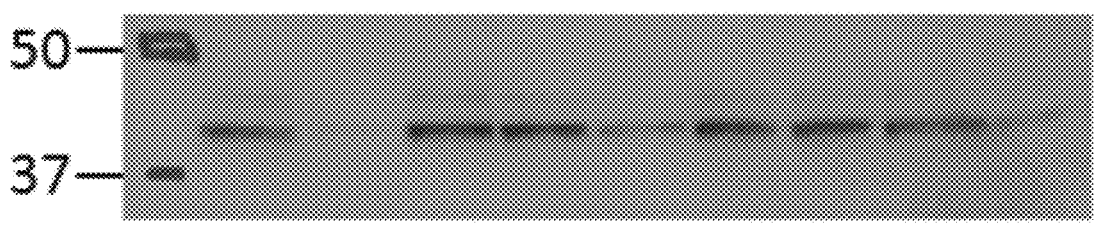
FIGS. 2A-C—Activation of ERK in human primary keratinocytes (HEKa) following treatment with BRaf inhibitors (0.3 µM, 1 µM or 3 µM C-1 or C-15).
Figure 2B:
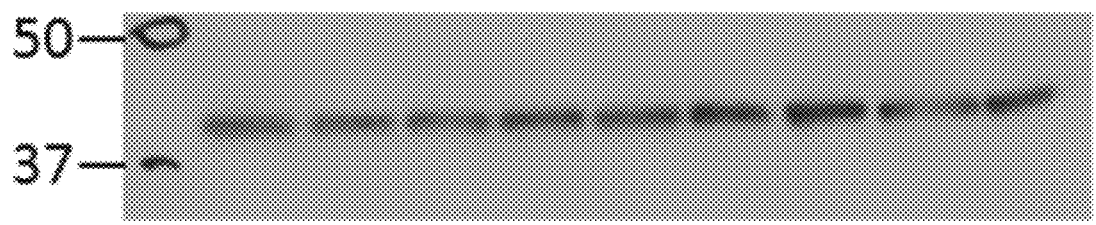
Figure 2C:
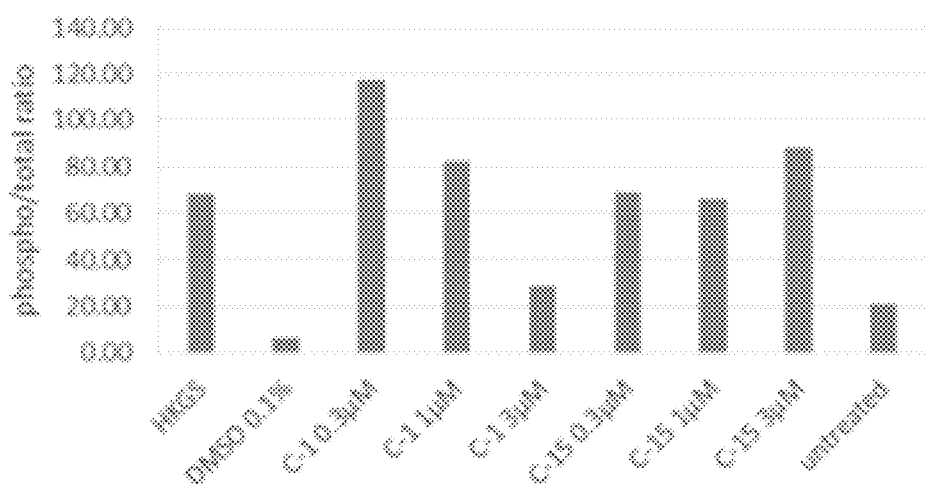

The results shown in FIGS. 2A-C demonstrate the activation of ERK (as determined by increase in relative amount of Phosphorylated ERK) in human primary keratinocytes (HEKa) following treatment with increasing amounts (0.3 µM, 1 µM or 3 µM) of C-1 or C-15 BRaf inhibitors.

Figure 3A:
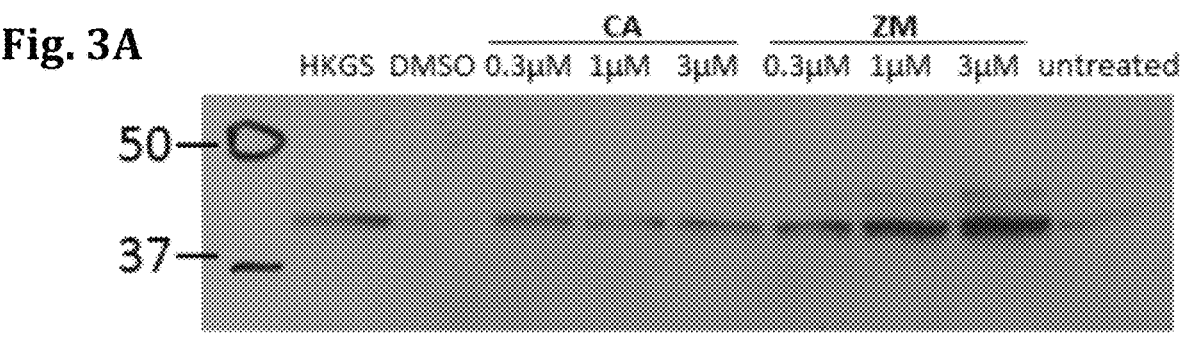
FIGS. 3A-C—Activation of ERK in human primary keratinocytes (HEKa) following treatment with BRaf inhibitors (0.3 µM, 1 µM or 3 µM C-A or ZM).
Figure 3B:
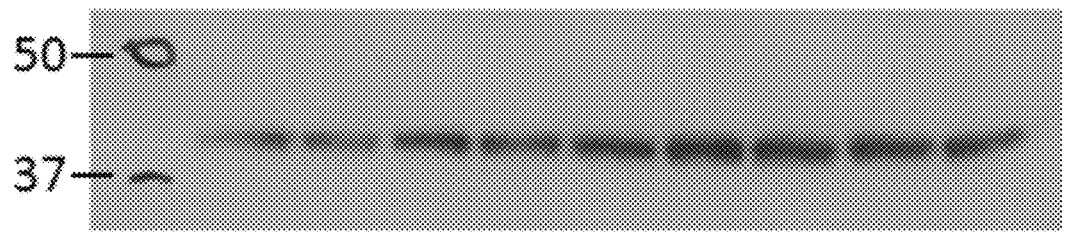
Figure 3C:
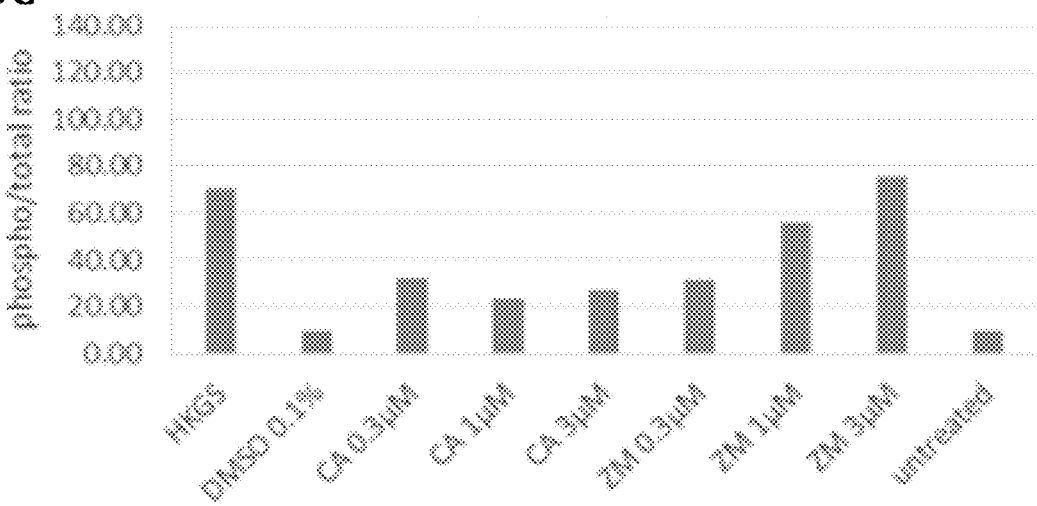

The results shown in FIGS. 3A-C demonstrate the activation of ERK (as determined by increase in relative amount of Phosphorylated ERK) in human primary keratinocytes (HEKa) following treatment with increasing amounts (0.3 µM, 1 µM or 3 µM) of C-A or ZM 336372 (ZM) BRaf inhibitors.

Figure 4A:
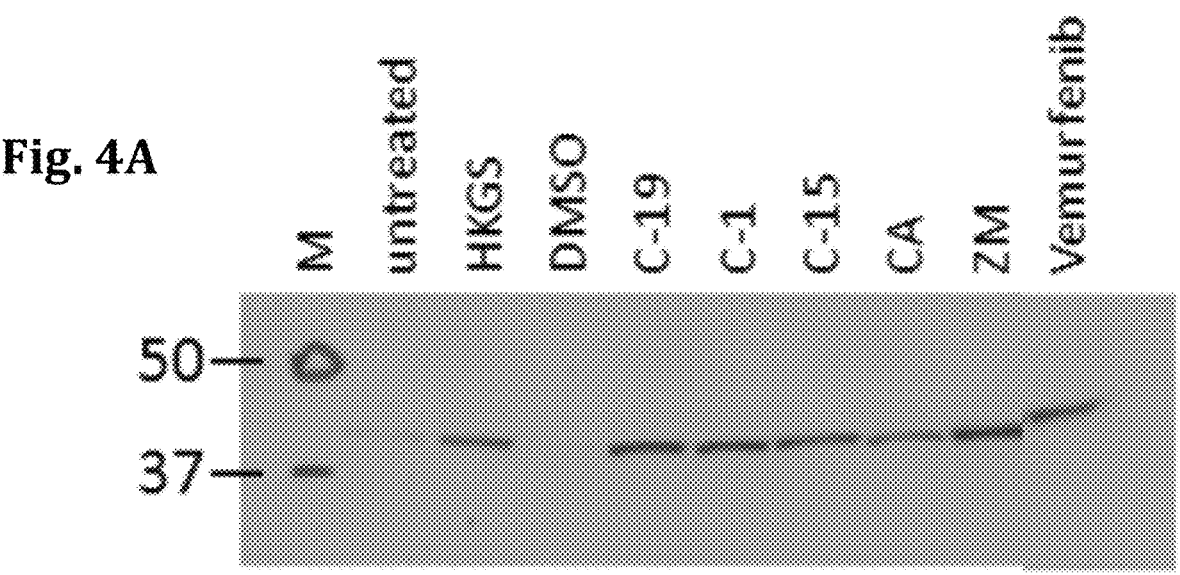
FIGS. 4A-C—Activation of ERK in human primary keratinocytes (HEKa) following treatment with various BRaf inhibitors (1 µM of C-19, C-1, C-15, CA or vemurafenib).
Figure 4B:
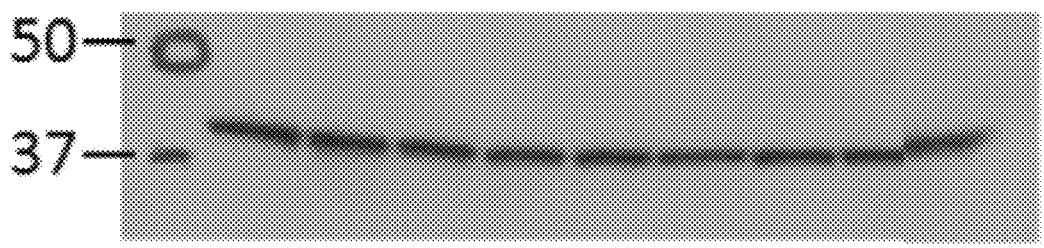
Figure 4C:
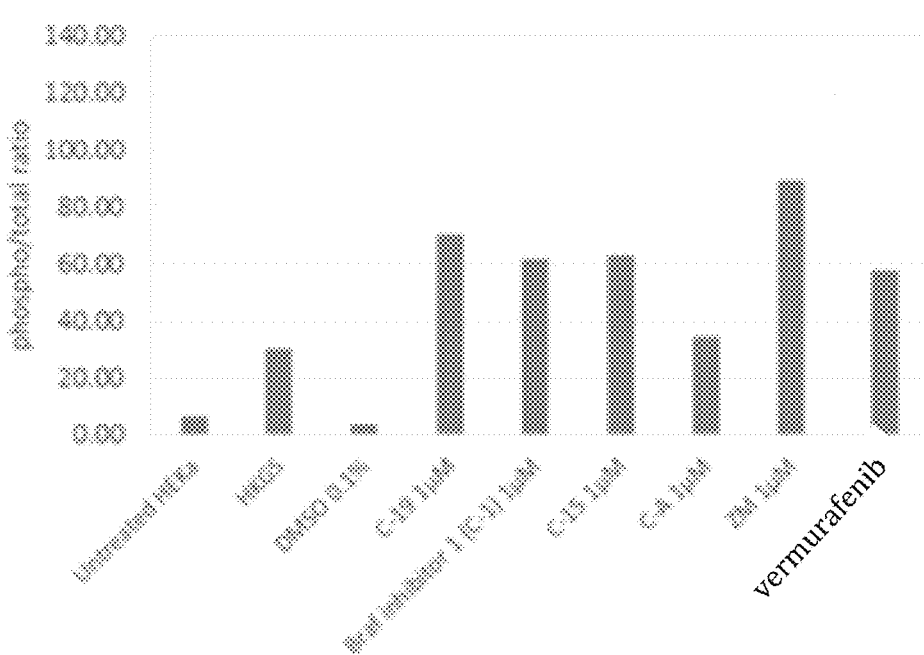

The results shown in FIGS. 4A-C demonstrate the activation of ERK (as determined by increase in relative amount of Phosphorylated ERK) in human primary keratinocytes (HEKa) following treatment with 1 µM of C-19, C-1, C-15, CA, or vemurafenib BRaf inhibitors or ZM (control, activator).

The results presented above herein demonstrate the paradoxical effect of various BRaf inhibitors on activation of downstream MAPK (ERK) in relevant keratinocytes cells. Further, the results demonstrate the varying efficacy of various inhibitors administered at varying dosages (concentration) in activating ERK.

Example 2—Effect of BRaf Inhibitors on Proliferation MIA PaCa2 KRAS Cells (MIA Paca Cells Harboring a Ras Mutation)

In order to demonstrate a durable effect of BRaf inhibitors, a proliferation assay using MIA Paca cell lines harboring a mutated KRas, was conducted Materials and Methods:

Materials—MIA PaCa2 KRAS cells (ATCC, CRM-CRL1420); DMEM (ATCC 30-2002); FBS (Biol. Industries, Cat. 04-007-1A); Horse serum (Biol. Industries, Cat. 04-004-1B), Antibiotics (P/S, Biol. Industries, Cat. 03-031-2B), Trypsin (Biol. Industries, Cat. 03-050-1A), Trypan Blue (Sigma T8154); DMSO (Sigma D2650), BRaf inhibitors ((C-1 MedChem Express (HY-14177); C-15; C-19; Vemurafenib (Royal Pharma)), ATPlite (Perkin Elmer, Cat. 6016941)

Cell Growth: On day 1, the cells are plated in culture media (DMED/FBS/Horse serum and antibiotics). Subsequently the cells are subcultured and incubated for 24 hours in a starvation media (i.e. serum depleted media). The test compounds (BRaf inhibitors) are then added to the cells at various concentrations and the cells are incubated (37° C. 5% $CO_2$) for additional 72 hours.

Proliferation Assay is performed using the ATPlite reagent, according to manufacturer protocol. The results are read using CLARIOstar (BMG) reader (Mode: Luminescence, program: ATPlite TOP, Measurement interval time [s]: 0.25-1.

Figure 5A:
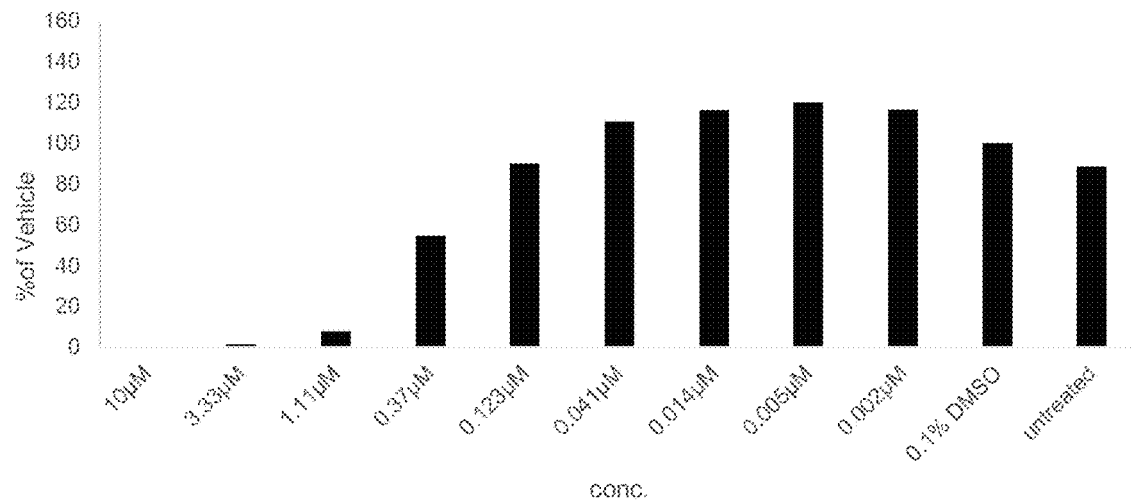
FIGS. 5A-D—Bar graphs showing the effect of BRaf inhibitors on proliferation of MIA PaCa2 KRAS cells. MIA-Paca2 cells were plated in growth media, and then starved for 24 hours in serum free media. BRaf inhibitors are then added to the cells at varying concentrations and 72 hours later, the proliferation of the cells is determined by the ATP-lite proliferation Assay.
Figure 5B:
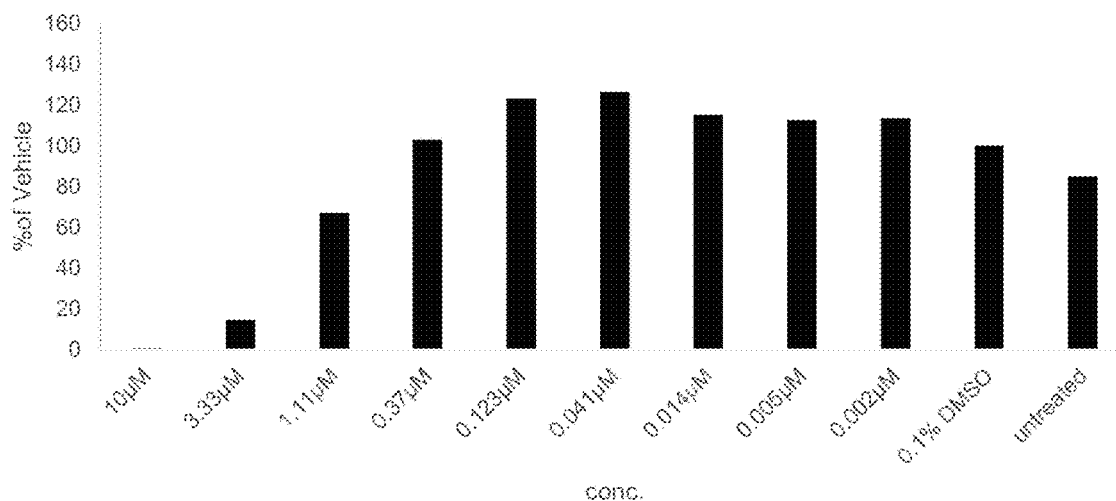
Figure 5C:
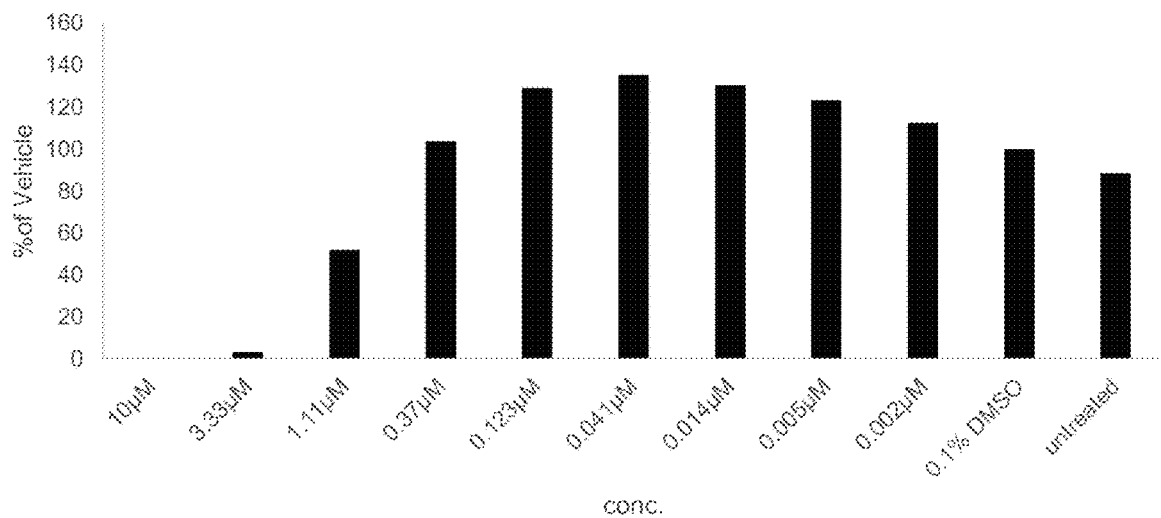
Figure 5D:
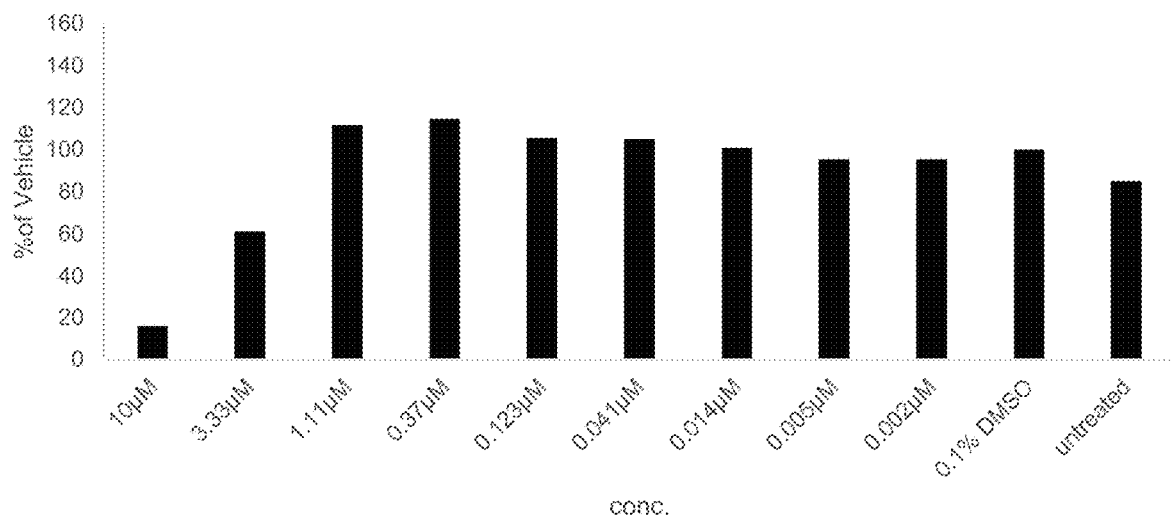

Results:

The results are presented in FIGS. 5A-D, which show the effect of varying concentration of various BRaf inhibitors on MIA-Paca2 cells proliferation. FIG. 5A illustrates the effect of the C-1 BRaf-inhibitor on the cells, when provided in varying concentrations. FIG. 5B shows the effect of varying concentration of the C-15 BRaf-inhibitor on the cells. FIG. 5C shows the effect of varying concentration of the C-19 BRaf-inhibitor on the cells. FIG. 5D shows the effect of varying concentration of Vemurafenib on the cells.

Example 3—Treating Cutaneous Condition in Subjects Treated with EGFR and/or PI3K Using BRaf-Inhibitors To treat cutaneous conditions induced by treatment of a subject with EGFR and/or PI3K inhibitor, subjects that have been diagnosed with such cutaneous conditions (i.e., subjects that have been or are being treated with EGFR inhibitor and/or with PI3K inhibitor) are administered with BRaf inhibitors, to treat said condition. As a control, a placebo treatment (vehicle) is provided.

Briefly, the treatment protocol includes the following steps:

Subjects—Patients treated with EGFR inhibitor (including cetuximab, panitumumab, necitumumab, gefitinib, erlotinib, lapatinib, vandetanib and/or osimertinib) or PI3K inhibitor (including buparlisib, dactolisib, pictilisib and/or idelalisib)). The patients are diagnosed with cutaneous conditions, (including acneiform).

Treatment—the subjects are treated for 6-20 weeks with a topical BRaf inhibitor in a suitable dosage form, on one body side, on face, neck and chest. The dosage form is a topical dosage form comprising 0.1-3% BRaf Inhibitor. Control—subjects are treated with a suitable placebo composition, which does not include a BRaf inhibitor as an active substance. When applied topically, the placebo treatment is performed on the body side which is not being treated.

During the treatment period, various parameters are tested, including, the rate of the cutaneous condition eruptions, the severity of the eruptions, the body location of the eruptions and other related cutaneous events. The body locations tested include face, neck and chest.

At the end of the trial treatment period, the tested parameters are determined by comparing the treated body regions with the placebo-treated regions, to determine treatment efficacy.

Example 4—Treating Cutaneous Condition in Subjects Treated with EGFR and/or PI3K Using BRaf-Inhibitors Systemically Administered To treat cutaneous conditions induced by treatment of a subject with EGFR and/or PI3K inhibitor, subjects that have been diagnosed with such cutaneous conditions (i.e., subjects that have been or are being treated with EGFR inhibitor and/or with PI3K inhibitor) are systemically administered with BRaf inhibitors, to treat said condition. As a control, a placebo treatment (vehicle) is provided to control treated subjects.

Briefly, the treatment protocol includes the following steps:

Subjects—Patients treated with EGFR inhibitor (including cetuximab, panitumumab, necitumumab, gefitinib, erlotinib, lapatinib, vandetanib and/or osimertinib) or PI3K inhibitor (including buparlisib, dactolisib, pictilisib and/or idelalisib)). The patients are diagnosed with cutaneous conditions (including acneiform).

Treatment—the subjects are treated for 6-20 weeks with a systemic BRaf inhibitor in a suitable dosage form. The dosage form is an oral dosage form comprising 200-1000 micrograms of BRaf inhibitor. Control—subjects are treated with a corresponding suitable placebo composition, which does not include a BRaf inhibitor as an active substance.

During the treatment period, various parameters are tested, including, the rate of the cutaneous condition eruptions, the severity of the eruptions, the body location of the eruptions and other related cutaneous events. The body locations tested include face, neck and chest.

At the end of the trial treatment period, the tested parameters are determined by comparing between treated and placebo treated subjects, to determine treatment efficacy.

What I claim is:

1. A method of treating a cutaneous condition induced by treatment with an Epidermal Growth like factor receptor (EGFR) inhibitor and/or a Phosphoinositide-3 Kinase (PI3K) inhibitor, the method comprising administration of a therapeutically effective amount of a BRaf inhibitor to a subject in need thereof,
wherein the cutaneous condition is selected from acneiform rash, papulopustular rash, abnormal scalp hair growth, abnormal facial hair growth, abnormal hair growth, abnormal eyelash growth, paronychia with or without pyogenic granulomas and telangiectasia,
wherein the BRaf inhibitor is selected from C-1, C-15, C-19, C-A and vemurafenib, and
wherein the BRaf inhibitor exhibits a paradoxical MAPK activation effect, thereby treating the cutaneous condition.

2. The method of claim 1, wherein the EGFR inhibitor is selected from: Iressa (gefitinib), Tarceva (erlotinib), Tykerb (Lapatinib), Erbitux (cetuximab), Vectibix (panitumumab), Caprelsa (vandetanib), Portrazza (necitumumab), Tagrisso (osimertinib) and combinations thereof.

3. The method of claim 1, wherein the PI3K inhibitor is selected from GDC-0980 (Apitolisib), GDC-0941 (Pictilisib), BAY 80-6946 (Copanlisib), BKM120 (Puparlisib), NVP-BEZ235 (Dactolisib), IPI 145 (Duvelisib), Idelalisib (GS-1101 or CAL-101), wortmannin and LY294002 and combinations thereof.

4. The method of claim 1, wherein the administration is selected from topical administration and systemic administration.

5. The method of claim 4, wherein the systemic administration is selected from enteral administration and parenteral administration.

6. The method of claim 4, wherein the systemic administration comprises oral administration.

7. The method of claim 4, wherein the topical administration comprises local administration to the skin of the subject.

8. A method of treating acneiform rash in a subject in need thereof, the method comprising administration of a pharmaceutical composition comprising a therapeutically effective amount of a BRaf inhibitor to the subject, wherein the BRaf inhibitor is selected from C-1, C-15, C-19, C-A and vemurafenib, and wherein the BRaf inhibitor exhibits a paradoxical MAPK activation effect, thereby treating acneiform rash in the subject.

9. The method of claim 8, wherein the administration is selected from systemic and topical.

10. The method of claim 9, wherein the composition is formulated in a dosage form selected from: ointment, cream, gel, hydrogel, spray, dermal patch, foam, lotion and liquid.

11. The method of claim 1 comprising administering topically a topical dosage form comprising 0.1-3% of the BRaf inhibitor.

12. The method of claim 1 comprising administering systemically an oral dosage form comprising 200-1000 mg of the BRaf inhibitor.

* * * * *